United States Patent [19]

Beech, Jr. et al.

[11] Patent Number: 5,324,865
[45] Date of Patent: Jun. 28, 1994

[54] DI-ISOPROPYL ETHER PRODUCTION

[75] Inventors: James H. Beech, Jr., Wilmington, Del.; Douglas Miller, Yardley, Pa.; Jorge L. Soto, Cranbury, N.J.; James A. Stoos, Blackwood, N.J.; Albert H. Wu, Medford, N.J.

[73] Assignee: Mobil Oil Corporation, Fairfax, Va.

[21] Appl. No.: 20,964

[22] Filed: Feb. 22, 1993

[51] Int. Cl.$^5$ .................. C07C 41/05; C07C 41/06
[52] U.S. Cl. .................. 568/695; 568/694; 568/697; 568/897
[58] Field of Search ............. 568/695, 694, 697, 897

[56] References Cited

U.S. PATENT DOCUMENTS

| | | | |
|---|---|---|---|
| 4,042,633 | 8/1977 | Woods | 260/614 |
| 4,182,914 | 1/1980 | Imaizumi | 568/697 |
| 4,666,563 | 5/1987 | Berg et al. | 203/56 |
| 4,857,664 | 8/1989 | Huang et al. | 568/695 |
| 4,906,787 | 3/1990 | Huang et al. | 568/697 |
| 5,138,102 | 8/1992 | Beech, Jr. et al. | 568/695 |
| 5,154,801 | 10/1992 | Harandi et al. | 203/43 |
| 5,162,591 | 11/1992 | Beech et al. | 568/695 |

*Primary Examiner*—Howard T. Mars
*Attorney, Agent, or Firm*—Alexander J. McKillop; Malcolm D. Keen; L. Gene Wise

[57] ABSTRACT

A process for production of diisopropyl ether by conversion of hydrocarbon feedstock containing propene, propane and $C_2-$ light gas components, including the steps of: optionally, prefractionating fresh feedstock containing propene, propane and $C_2-$ light gas components to provide a reactor feedstream rich in propene; contacting the feedstock and water in a catalytic reactor with acidic catalyst under olefin hydration and etherification conditions; and recovering from the catalytic reactor a liquid reactor effluent stream containing diisopropyl ether, isopropanol, water, unreacted propene, propane and $C_2-$ light gas components. Improved operation is achieved by separating the liquid effluent stream in a vertical stripper column; recovering an overhead vapor stream containing propene, propane and $C_2-$ light gas components from the stripper column; cooling the overhead vapor stream to provide a reflux stream rich in condensed propene and propane; removing the $C_2-$ light gas components from condensed; recycling the reflux stream to an upper contact portion of the stripper column; and recovering a predominantly C3 recycle stream from the upper contact portion of the stripper column. Optionally, the C3 recycle stream may be passed to the to the prefractioning step for propene enrichment with fresh feedstock.

14 Claims, 2 Drawing Sheets

FIG. 1

DI-ISOPROPYL ETHER PRODUCTION

BACKGROUND OF THE INVENTION

This invention relates to olefin hydration, especially for production of di-isopropyl ether (DIPE) from $C_{3+}$ olefinic feedstock. Particularly, the invention relates to a novel technique for recovering DIPE product and unreacted light hydrocarbons from reactor effluent.

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_{3+}$ aliphatic stream rich in propene and propane. The petrochemicals industry also produces mixtures of light olefin streams in the $C_2$-$C_7$ molecular weight range and the conversion of such streams or fractions thereof to alcohols and/or ethers can also provide products useful as solvents and blending stocks for gasoline. Feedstocks of particular interest are light hydrocarbon streams rich in propene, which are often accompanied by significant amounts of propane, ethene, ethane and other light gases.

Adapting available refinery feedstock to produce these oxygenates simultaneously as octane enhancers can involve two different olefin hydration and etherification processes, i.e. propene hydration-etherification to give DIPE and IPA. Accordingly, a challenge is provided to explore these processes to discover how they may be integrated in a manner more beneficial to the production of high octane gasoline.

Catalytic hydration of olefins to provide alcohols and ethers is established technology for production of the IPA and DIPE and is of significant commercial importance. Olefin hydration employing medium pore and large pore zeolite catalyst is a known synthesis method. Recently, processes for the direct hydration of olefins to provide alcohols and ethers using porous shape selective metallosilicate zeolite catalyst, such as zeolite Beta have been disclosed in U.S. Pat. Nos. 4,857,664 (Huang et al.), 4,886,918 (Sorensen et al) and 5,138,102 (Beech et al), incorporated herein by reference. Prior processes for hydrating olefins have often been found to be inefficient with regard to catalyst life. Maldistribution of water and hydrocarbon reactants may cause deactivation, especially with solid metallosilicate catalysts having large pores (i.e. 7+ Angstroms) or medium pores (5-7 A°).

It is a main object of this invention to provide an improved process for production of oxygenated hydrocarbons by olefin hydration, such as alcohols and/or ethers in a more economical manner and with improved yields of ethers. It is a further object to provide novel reactor effluent separation and recovery techniques for use in DIPE reactor systems.

SUMMARY OF THE INVENTION

A novel process has been discovered for production of ether/alcohol from lower olefins. In the preferred embodiments, di-isopropyl ether (DIPE) is produced by hydration and etherification of propene-rich feedstock containing $C_2$- components, which comprises contacting the propene feedstock, IPA and water in a catalytic reactor containing porous solid acidic catalyst under olefin hydration and etherification conditions. Improved operation is obtained by recovering a net liquid effluent stream from said catalytic reactor containing diisopropyl ether, isopropanol, water, unreacted propene, propane and $C_2$- light gas components, and separating the liquid effluent stream in a vertical stripper column having a lower reboiler portion and an upper contact portion, thereby recovering an overhead vapor stream containing propene, propane and $C_2$- light gas components from the stripper column. By cooling the overhead vapor stream to provide a reflux stream rich in condensed propene and propane; removing the $C_2$- light gas components from condensed reflux; recycling the reflux stream to the upper contact portion of the stripper column; a predominantly C3 recycle stream is recovered from the upper contact portion of the stripper column, and at least a portion of the C3 recycle stream can be passed directly or indirectly to the catalytic reactor.

For feedstocks rich in propane and/or $C_{4+}$ components, fresh feedstock is prefractionated to provide a reactor feedstream rich in propene; and the C3 recycle stream may be prefractionated economically with fresh feedstock.

These and other advantages and features of the invention will be seen in the description and drawing.

DETAILED DESCRIPTION OF THE INVENTION

The preferred embodiments of the invention are described with reference to refinery grade propene feedstocks and zeolite catalysts. Metric units and parts by weight are employed unless otherwise indicated.

The olefins hydration and etherification process employs the reaction of propylene with water catalyzed by strong acid to form isopropanol. Reaction may be allowed to continue in the hydration zone to form di-isopropyl ether. The operating conditions of the olefin hydration and etherification reaction step include a temperature of about 50° to 450° C., preferably from 100° to 250° C. and most preferably from 120° to 220° C. The total pressure is about 700 to 24000 kPa (100 to about 3500 psi, preferably 500–2000 psi). Water to olefin reactant concentrations are maintained at mole ratio of about 0.1 to 30, preferably 0.1-5.

The preferred catalytic methods for making DIPE employ porous solid acid catalysts, such as zeolites Beta, Y, ZSM-35 and/or MCM-22 aluminosilicate. The preferred hydration/etherification catalyst comprises acidic, shape selective porous zeolite having a pore size of about 5–8 Angstroms, such as aluminosilicate zeolite Beta. Also, MCM-22, having pores similar to zeolite Beta and ZSM-5, is known for etherification catalysis, as disclosed by Marler et al in U.S. Pat. No. 5,105,023.

DIPE etherification conditions may vary widely in choice of temperature, pressure and reaction time. The preferred method reacts propene with water in an adiabatic downflow reactor containing a fixed bed of catalyst, such as zeolite Beta, at 100° to 250° C. and pressure of at least 4000 kPa. However, it is understood that the unit operations described herein can be conducted with any number of specific process steps within the skill of the art.

The olefin hydration and etherification reaction step is carried out in liquid phase or supercritical dense phase in continuous manner using a fixed bed flow reactor. Weight hourly space velocity, based on catalyst weight is maintained in the range of 0.1 to 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature, phase behavior and flow parameters. It is ordinarily desirable to recover any unreacted olefin and recycle it to the reactor. Unconverted isopropanol recovered from the final reactor effluent may also be recycled advantageously for further conversion to ether.

Figure 1:
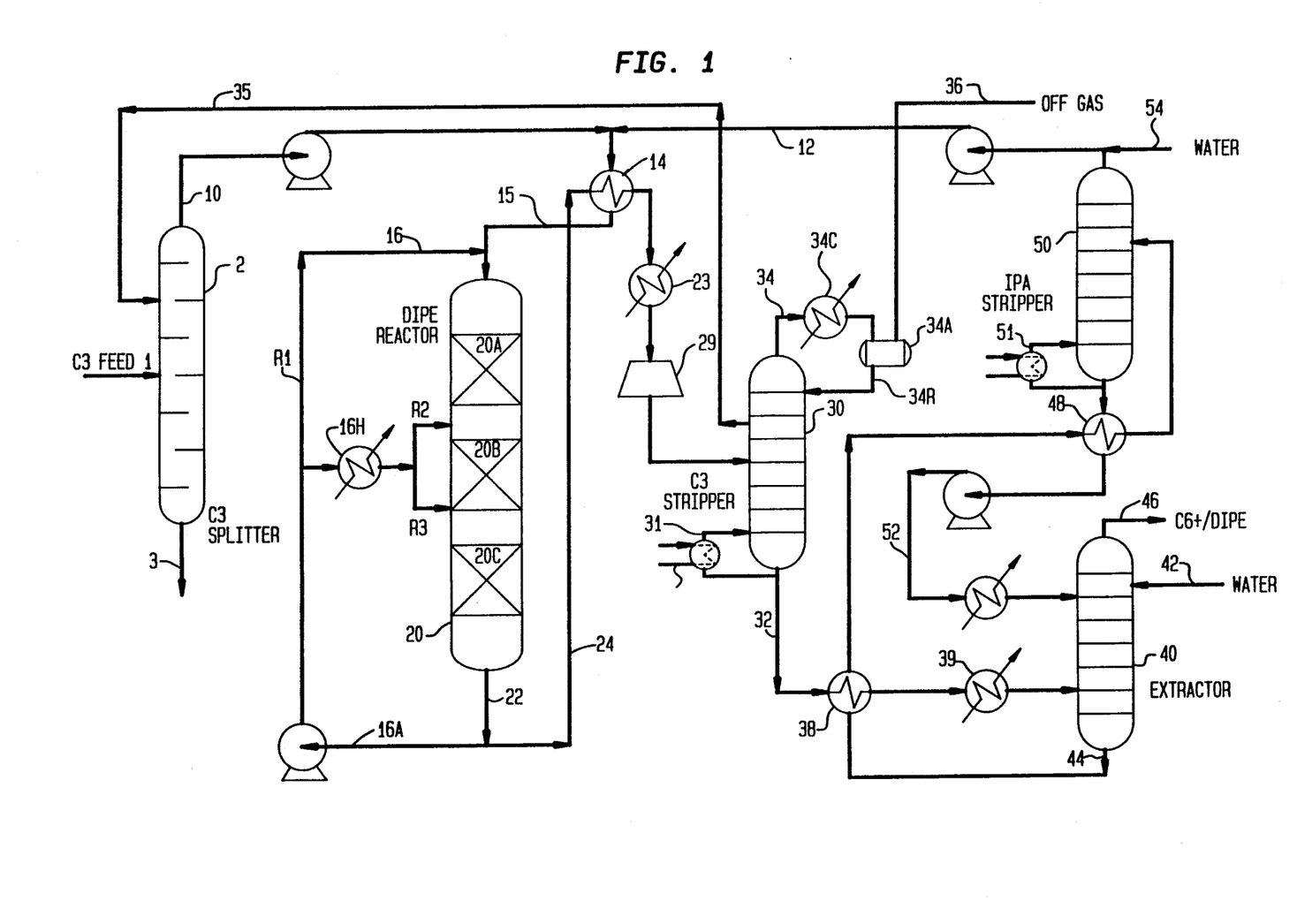
FIG. 1 is a schematic process flow diagram of the improved process.

Referring to FIG. 1 of the drawing, a process flow diagram depicts production of diisopropyl ether by hydration of fresh olefinic feedstock stream, which is introduced as a propane-propene mixture via inlet 1 to feed splitter tower 2 to recover a propane-rich bottoms stream 3, which will also contain any $C_4+$ components in the feedstock. An overhead stream consisting essentially of propene ($C_3=$, propylene) is pumped along with water from stream 12 through heat exchanger 14 to bring the reactants and recycle stream 16 to the process conditions for etherification in vertical reactor 20 in contact with porous solid acidic olefin hydration catalyst.

The reactor vessel 20 contains a series of fixed bed adiabatic hydration reaction zones 20A, 20B, 20C maintained under olefin hydration conditions. Static mixers and liquid distributors may be employed before each bed to promote operation in a single homogeneous phase, as localized high concentrations of water or propene are known to deactivate acidic catalysts (both zeolites and resins). Preferably, at least one hydration reaction zone contains porous zeolite catalyst, such as zeolite Beta.

A fluid handling system is operatively connected for recovering a liquid reactor effluent stream 22 from the last zone 20C. This can be achieved by splitting effluent stream 22 into a liquid product recovery stream 24 and a liquid recycle stream 16A, which is recycled to the multizone reactor 20 as a plurality of flow-controlled recycle streams R1, R2, R3. Heat exchanger 16H cools the interstage quench streams R2, R3 below the process temperature, thus balancing the adiabatic heat of reaction from the preceding zone. Reactor 20 is operated continuously by passing the liquid recycle stream 16A for direct mixing with the reactor feedstream. Reaction temperature can be controlled in zones 20B, 20C by varying the degree of cooling and/or flow rate of the recycle stream in unit 16H. Typically, the reactor effluent and liquid product recovery stream consist essentially of 0.5-10 wt. % water, 20-60 wt. % propene, 20-30 wt. % di-isopropyl ether, 10-15 wt. % isopropanol, and various amounts of unreacted light $C_3$- materials, such as 5 to 40 wt. % total $C_3$-. Typically, propane and $C_2$- components comprise 0.1-10 wt. % and 3-40 wt. %, respectively.

The amount of unfractionated liquid recycle stream 16 may be sufficient to maintain a substantially homogeneous single liquid reaction phase in the primary hydration zone 20A under reaction conditions. Use of DIPE, IPA containing product for quench will also promote single phase operation. The first liquid product stream 24 is passed via exchangers 14, 23 and fluid handling unit 29 to the product fractionation system, as described.

Effluent stream 24 is fractionated in the product recovery system first in C3 stripper column 30, equipped with reboiler means 31, to recover a liquid ether-rich stream 32. The column overhead vapor stream 34 is cooled in condenser means 34C to condense a large portion of C3 and C2 hydrocarbons for recycle via accumulator means 34A and recycle means 34R. Advantageously, a high recycle rate is maintained in the range of 25:1 to 100:1, preferably about 75:1. A propene-rich C3 stream 35 is withdrawn in a upper portion of column 30 for recycle to tower 2 via line 35. Light hydrocarbons may be purged from the system via line 36.

It is advantageous to recover isopropanol for recycle to the reactor to provide isopropanol by-product stream for further conversion to di-isopropyl ether. In the DIPE system depicted, unfractionated liquid recycle stream 16A is passed to reactor 20 at a high rate, usually about four times the total weight of propene and water reactants in the product recovery stream 24; the exact quantity depends on conversion targets, feed properties, etc.

Ether-rich stream 32 containing by-product isopropanol, unreacted propene, water and $C_6+$ hydrocarbon oligomer is further separated after passing through heat exchangers 38, 39 to extractor unit 40, where it is contacted with feed water 42 and/or water recycle stream 52 to extract isopropanol in an aqueous phase 44. A wet product stream 46 consisting essentially of DIPE and by-product $C_6+$ propene oligomer is recovered from the extraction unit 40, and can be further process to remove excess water. The extract phase 44 is passed via exchangers 38, 48 to IPA stripper column 50 to obtain an overhead isopropanol recycle stream 12. Makeup water stream 54 may be added to the IPA recycle stream 12, as required to maintain the reactor conditions. A portion of the stripper bottom stream is passed through reboiler means 51 and liquid aqueous stream 52 is recycled through the extraction loop via unit 40.

The IPA extraction loop may be operated with extractants other than water. For instance, carbon dioxide has appropriate characteristics under supercritical conditions to extract IPA and produce a DIPE-rich raffinate stream analogous to stream 46. Such an alternative extraction loop may require changes in the manner of water addition. Carbon dioxide extraction can be effected at about 40°-60° C. and 10,000-13,000 kPa pressure. IPA is readily recovered from the extractant by flashing to create a separate $CO_2$ gaseous phase, which can be recycled by compression. Conditions and operating techniques suitable for IPA/water and other systems can be found in McHugh and Krukons, *Supercritical Fluid Extraction*, 1986. In addition to IPA recovery, supercritical extraction can be employed in a multistage system for removing water from stream 46 to provide a dry DIPE product containing a minor amount of C6 dimer suitable for gasoline blending.

The process flow scheme for olefin hydration to ethers over a zeolite Beta catalyst as disclosed utilizes product recycle and reactor quench for improved catalyst life and temperature control. A preferred system utilizes three catalyst beds in a single vertical reactor shell with mixing with inter-bed quench to reduce cost while controlling system phase behavior in comparison to other designs (tubular reactor).

Improved catalyst life and yield benefits are realized when recycling reactor product (pumparound) for propene hydration to di-isopropylether (DIPE) over typical porous acid solid catalyst. Product pumparound is advantageous as a means of controlling reactor temperature rise and therefore reduces equipment cost, as compared to a conventional isothermal tubular reactor or the like. This is achieved in the preferred reactor system configuration by providing fluid control means for splitting a first liquid effluent stream into a liquid product recovery stream and a liquid recycle stream, means for cooling at least a portion of the liquid recycle stream, and means for passing the cooled liquid recycle stream as interstage quench between serial fixed bed hydration zones in the catalytic reactor for controlling reaction temperature. Preferably, total liquid recycle is combined with fresh feed at a weight ratio of about 2:1 to 10:1 recycle:feed, and the liquid product stream is separated into at least two streams for recycle to separate reaction zones, and cooled liquid recycle is injected between separated fixed catalyst beds.

The use of the product recycle for inter-bed quench eliminates inter-reactor coolers; while giving benefits in control of phase behavior. With three beds contained in a single reactor vessel, lower cost may be achieved. This preferred process design, which is suitable for commercial design, utilizes feed purification, product recycle, and reactor quench for hydration of propene to DIPE to achieve high propene conversion (up to −95% overall). The design also takes advantage of reactor recycle and quench with interstage mixing-distribution to provide reduced catalyst aging and reactor temperature control (heat removal).

The integration techniques and process improvements of this invention result in unexpected benefits in process performance. Reduced water operation greatly improves the catalyst regenerability and ultimate life. The specific nature of the DIPE/C3/C2 system lends itself to in-situ concentration and removal of C2 and C4.

Figure 2:
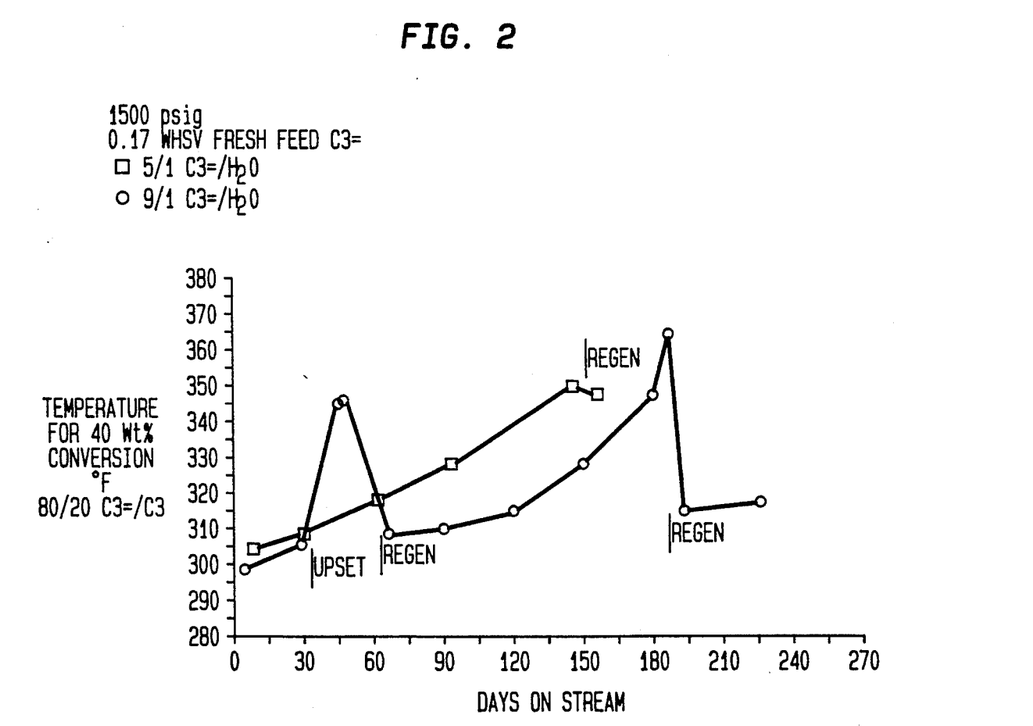
FIG. 2 is a graph of reactor temperature, comparing the effect of water content on catalyst activity.

The significance of propene/water ratio in the reaction mixture is demonstrated in FIG. 2, where reactor temperature required for 40% conversion of propene is plotted for continuous DIPE synthesis. Where the ratio of $C_3=/H_2O$ was maintained at 5/1, catalyst deactivation required reaction temperature to be increased in order to maintain constant $C_3=$ conversion, while operating without effluent pumparound. Following oxidative regeneration, the catalyst recovery was insignificant.

In the comparative run at 9/1 propene/water, operating with single phase operation with low water content and effluent pumparound, the catalyst was regenerable.

The optimum propene/water ratio is found between 3/1 and 4.5/1 (1.5-2.2 times stoichiometric). Lower water content can lead to increased oligomer formation and catalyst coking.

In fixed bed hydration of propene to di-isopropyl ether (DIPE), catalyst aging has been found to limit cycle length and catalyst life during single pass operation. When effluent recycle with mixing and quenching are employed, propene conversion and DIPE yield increase and aging is significantly reduced. This effect is unexpected, since pump-around type of reactor operation (i.e., back mixed) generally reduces conversion compared to plug flow (single pass). Catalyst life is increased compared to conventional process flow schemes. Product pumparound recycle is ordinarily expected to lower yields (back-mixed versus plug flow) and reduce catalyst life (coke/polymer formation). The opposite occurs in both instances.

This advantage in yield and catalyst aging is unexpected. Product recycle is believed to improve overall distribution in the reactor due to higher flux and improving phase behavior (a single liquid phase versus water-rich and water-lean phases). The increased DIPE at the reactor inlet might act as a solvent to remove coke precursors. Temperature control by product recycle quench is also a primary benefit for process with a small window of operation.

This flow scheme provides significant benefits beyond simple heat control. It is possible to adjust pumparound composition by adjusting reactor effluent temperature, separating out a water rich phase, and recycling a separated ether-rich phase which may further improve performance. This same effect in water reduction might also be accomplished by reducing the water content or amount of the IPA/water recycle from distillation.

A theoretical explanation for the observed increase in yields results from the strong solvents isopropanol/ether saturating the catalyst pores. This prevents the formation of any separate water or olefin phases in the pores during operation. The aqueous or hydrocarbon phases can cause catalyst deactivation. The water phase may attack the crystalline structure of the catalyst, while a highly olefinic phase would deactivate the catalyst via rapid coke formation. The isopropanol/ether mixture also allows controlled quantities of water and propene to be present homogeneously in the catalyst pores, which allows the reactions to proceed properly at reaction temperature. For the recycle technique to be effective, the recycled liquid must dissolve the water and olefin present in fresh feedstock and the quench must be used with good mixing and distribution. The reactor feed contents must be within carefully adjusted ratios to maintain single phase operation, maintain product selectivity and balance IPA production with IPA losses from the system. The IPA distillation and recycle is critical to maintaining these ratios. Previous work had shown reagent grade DIPE could be dried via distillation or sorption. We have determined that fuel grade DIPE (>3 wt. % oligomer) can be dried by distillation more easily than reagent grade DIPE. In addition, the oligomers do not foul the sorbents so drying by sorption could also be used.

The DIPE process of this invention differs from traditional single reaction ether processes, such as dry reaction of a primary alkanol with an alkene in that the present catalyst is exposed to water (the other processes use alcohol feed to introduce the oxygen containing reactant). In the present process, catalyst deactivation occurs both by hydrolytic damage and by pore plugging via coke and/or polymer deposition. Reducing the water content below stoichiometric to obtain single fluid phase operation reduces permanent hydrolytic damage but increases the rate of deactivation via coking. Catalyst activity lost due to coking during operation with low water content can be substantially recovered with little permanent hydrothermal damage. By contrast, catalyst deactivation due to exposure to high concentrations of water may not be recovered. The result is a significant net increase in catalyst life with low water operation. For oxidative regeneration two or more DIPE reactor vessels should be used to assure continuous operation. While one reactor is producing DIPE the other can be undergoing regeneration in-situ. Alternatively an offsite regeneration procedure could be used.

In the following examples, 65% zeolite Beta is used in extrudate form with alumina binder; however, other binders such as silica, zirconia, etc may be used. Continuous runs are made, with propene weight hourly space velocity of [0.33] /hr charged to catalyst. Unless otherwise indicated, reaction conditions include reactor inlet temperature of about [165° C.] and pressure of [10,000] kPa.

FIG. 2 compares two reactor system configurations, one at high water content and one at low water content with pump-around and single phase conditions always maintained. The catalyst from the first experiment is not regenerable, whereas the catalyst from the second experiment is regenerable. In addition to high water content, the first run is operated without pump-around or procedures to maintain single phase operation. Phase equilibria data indicate two liquid phases are present during this experiment, because of the high water content. The second run uses a Beta catalyst with low water, pump-around and single phase operation. Operation at very low water content is also undesirable as this leads to high oligomer and coke production. The optimal propene/water mole ratio is between 3 and 4.5 (2 is stoichiometric for hydration of propene to isopropanol).

Operation at very low water levels is not generally taught in the prior art. The unexpected benefit comes from regenerability of preferred catalysts, such as Zeolite Beta, which often are not substantially regenerable at higher water levels above 10 wt. % of the reaction mixture. In conventional IPA synthesis processes high water content is employed, typically 25-50 times the propene feed.

Due to the relatively low equilibrium conversion of propene (~65%), it is desirable to recycle the unconverted propene. However, commercial feed streams contain trace amounts of C2- material, such as ethene, ethane and/or methane, which would accumulate in the recycle loop. Purging of this material results in losses of valuable propene. Allowing the C2- to accumulate before purging results in poor performance of the separation systems. Using lean oil absorbers to remove the C2- material introduce cost, complexity and potential catalyst poisons.

Purification of the fresh feed is ineffective, because trace levels of C2's or other light components will build up and require purging with subsequent loss of propene. In practice typical of IPA plants, the purged material is sent to a gas plant, however, this is expensive as it involves reprocessing large volumes of propene.

As shown in Tables 1-4, the present invention utilizes a propane/propene (P/P) stripper to concentrate the C2- material prior to purging. As demonstrated in Table 2 a 20% increase in DIPE production is achieved with the present invention, as compared to a simple purge, Table 1. This invention results in a 137% savings in P/P splitter utilities compared to allowing the C2- material to accumulate, Table 3. Table 3 demonstrates the poor performance of the P/P splitter at higher pressure. However, due to the relative volatility differences of DIPE and propene, performing the C2- concentration in the P/P stripper at high pressure does not adversely impact the operation of this column. High pressure also allows for elimination of a recycle pump for stream 35.

Unit Operations for P/P Stripper—Flow rates are given in pound-moles (lb-mols) per hour. Stripper (30) is exemplified for the process flow rates of Table 2 as a vertical column with 22 trays for contact stages, designated 1-22 from top to bottom. Liquid stream 24 (1059.0 lb-mols; 411 psia, 223° F.) from the reactor is fed to tray 15 in a mid portion of the column, and liquid product stream 32 (417.3 lb-mols; 412 psia, 3.55° F.) is recovered from bottom tray 22. A side draw is made to remove liquid C3 stream 35 (1059.0 lb-mols; 410 psia, 145° F.) from tray 5. Overhead vapor stream 34 (2387.2 lb-mols; 400 psia, 103.4° F.) is substantially condensed to provide reflux stream 34R (2356.1 lb-mols) at a molar reflux ratio of 75.7:1 and a C2- rich vapor purge stream 36 (31.1 lb-mols) is removed from the system. The reflux as a molar ratio of liquid feed is 1.56:1.

Improved stripper design with large reflux serves to concentrate both the overhead and sidedraw streams, with placement of the sidedraw in the top 25%-10% of the column contributing to a balancing of concentration of C3 components between recycle and purge streams. Excessive amounts of C2- light gas components in the stripper overhead would require condenser coolant to be less than a standard 100° F. cooling water stream. The side draw stream 35 is passed to the prefractionation P/P splitter unit 2, which can be operated at 1800 kPa (about 265 psia) for significant energy savings.

The stripper purge stream has an optimal C2- light gas 40-70 wt. %. At higher light gas content higher pressure and refrigeration, are required to condense the overhead stream. At lower light gas content a substantial amount of propylene may be lost to the offgas. Location of the side draw is optimized to allow the single reflux stream 30 to produce the desired purity for both streams 35 and 36. The use of the stripper to remove light gas components also improves reactor performance by increasing propene purity and phase density, which influence reaction rates favorably.

TABLE 1

| | Simple Purge Design | | | | | |
|---|---|---|---|---|---|---|
| Stream No. | P/P Splitter Feed <1> | $C_3$ Recycle <35> | $C_3^+$ Off <3> | $C_3^=$ Rich <10> | IPA/ $H_2O$ <12> | $R_X$ Effluent <24> |
| lb-mol/hr | | | | | | |
| $C_2=$ | 0.7 | 1.3 | 0.0 | 2.0 | 0.0 | 2.0 |
| $C_2$ | 17.6 | 43.2 | 0.0 | 60.8 | 0.0 | 60.8 |
| $C_3=$ | 449.7 | 441.1 | 5.7 | 885.2 | 0.0 | 526.7 |
| $C_3$ | 136.4 | 271.3 | 89.9 | 319.2 | 0.0 | 319.2 |
| $C_4=$ | 14.7 | 0.0 | 14.7 | 0.0 | 0.0 | 0.0 |

TABLE 1-continued

Simple Purge Design

| | | | | | | |
|---|---|---|---|---|---|---|
| C6=+ | 0.0 | 0.0 | 0.0 | 0.0 | 0.0 | 22.2 |
| DIPE | 0.0 | 0.0 | 0.0 | 0.0 | 7.1 | 162.0 |
| IPA | 0.0 | 0.0 | 0.0 | 0.0 | 133.9 | 138.3 |
| H2O | 0.0 | 0.1 | 0.0 | 0.0 | 205.5 | 46.3 |
| Total | 619.1 | 757.1 | 110.3 | 1267.2 | 346.5 | 1277.5 |

| Stream No. | $R_x$ Recycle <16A> | $C_2$ Purge <36> | Bottoms <32> | DIPE Raffinate <46> | Water Feed <44> | Stripper Bottoms <52> |
|---|---|---|---|---|---|---|
| C2= | 8.0 | 0.7 | 0.0 | 0.0 | 0.0 | 0.0 |
| C2 | 243.2 | 17.6 | 0.0 | 0.0 | 0.0 | 0.0 |
| C3= | 2106.8 | 85.2 | 0.4 | 0.4 | 0.0 | 0.0 |
| C3 | 1276.8 | 47.5 | 0.4 | 0.4 | 0.0 | 0.0 |
| C4= | 0.0 | 0.0 | 0.0 | 0.0 | 0.0 | 0.0 |
| C6=+ | 88.8 | 0.0 | 22.2 | 22.2 | 0.0 | 0.0 |
| DIPE | 648.0 | 0.0 | 162.0 | 154.9 | 7.1 | 0.0 |
| IPA | 553.0 | 0.0 | 138.3 | 5.1 | 133.6 | 0.4 |
| H2O | 185.2 | 0.0 | 46.2 | 4.8 | 1364.6 | 1222.9 |
| Total | 5110.0 | 150.9 | 369.5 | 187.9 | 1505.3 | 1223.3 |

| Stream No. | Water Feed <42> | Water Feed <54> |
|---|---|---|
| C2= | 0.0 | 0.0 |
| C2 | 0.0 | 0.0 |
| C3= | 0.0 | 0.0 |
| C3 | 0.0 | 0.0 |
| C4= | 0.0 | 0.0 |
| C6=+ | 0.0 | 0.0 |
| DIPE | 0.0 | 0.0 |
| IPA | 0.0 | 0.0 |
| H2O | 100.8 | 63.4 |
| Total | 100.8 | 63.4 |

TABLE 2

Improved Process Design

| Stream No. | P/P Splitter Feed <1> | $C_3$ Recycle <35> | $C_3^+$ Off <3> | $C_3^=$ Rich <10> | IPA/ $H_2O$ <12> | $R_x$ Effluent <24> |
|---|---|---|---|---|---|---|
| lb-mol/hr | | | | | | |
| C2= | 0.7 | 0.6 | 0.0 | 1.3 | 0.0 | 1.3 |
| C2 | 17.6 | 43.2 | 0.0 | 60.8 | 0.0 | 60.8 |
| C3= | 449.7 | 625.2 | 7.9 | 1067.1 | 0.0 | 634.9 |
| C3 | 136.4 | 389.9 | 132.1 | 394.1 | 0.0 | 394.1 |
| C4= | 14.7 | 0.0 | 14.8 | 0.0 | 0.0 | 0.0 |
| C6=+ | 0.0 | 0.0 | 0.0 | 0.0 | 0.0 | 26.7 |
| DIPE | 0.0 | 0.0 | 0.0 | 0.0 | 5.7 | 192.4 |
| IPA | 0.0 | 0.0 | 0.0 | 0.0 | 136.0 | 141.4 |
| H2O | 0.0 | 0.1 | 0.0 | 0.0 | 247.9 | 56.0 |
| Total | 619.1 | 1059.0 | 154.8 | 1523.3 | 389.6 | 1507.5 |

| Stream No. | $R_x$ Recycle <16A> | $C_2$ Purge <36> | Bottoms <32> | DIPE Raffinate <46> | Water Feed <44> | Stripper Bottoms <52> |
|---|---|---|---|---|---|---|
| C2= | 5.2 | 0.7 | 0.0 | 0.0 | 0.0 | 0.0 |
| C2 | 243.2 | 17.6 | 0.0 | 0.0 | 0.0 | 0.0 |
| C3= | 2539.6 | 9.1 | 0.6 | 0.6 | 0.0 | 0.0 |
| C3 | 1576.4 | 3.7 | 0.4 | 0.4 | 0.0 | 0.0 |
| C4= | 0.0 | 0.0 | 0.0 | 0.0 | 0.0 | 0.0 |
| C6=+ | 106.8 | 0.0 | 26.7 | 26.7 | 0.0 | 0.0 |
| DIPE | 769.6 | 0.0 | 192.4 | 186.8 | 5.6 | 0.0 |
| IPA | 565.6 | 0.0 | 141.4 | 6.2 | 135.6 | 0.5 |
| H2O | 224.0 | 0.0 | 55.8 | 5.8 | 1656.4 | 1498.9 |
| Total | 6030.0 | 31.1 | 417.3 | 226.6 | 1797.6 | 1499.4 |

| Stream No. | Water Feed <42> | Water Feed <54> |
|---|---|---|
| C2= | 0.0 | 0.0 |
| C2 | 0.0 | 0.0 |
| C3= | 0.0 | 0.0 |
| C3 | 0.0 | 0.0 |
| C4= | 0.0 | 0.0 |
| C6=+ | 0.0 | 0.0 |
| DIPE | 0.0 | 0.0 |

TABLE 2-continued

| | Improved Process Design | |
|---|---|---|
| IPA | 0.0 | 0.0 |
| H2O | 107.8 | 90.1 |
| Total | 107.8 | 90.1 |

TABLE 3

Accumulate C2's Prior to Purge

| Stream No. | P/P Splitter Feed <1> | C$_3$ Recycle <35> | C$_3$+ Off <3> | C$_3$= Rich <10> | IPA/ H$_2$O <12> | R$_X$ Effluent <24> |
|---|---|---|---|---|---|---|
| lb-mol/hr | | | | | | |
| C2= | 0.7 | 8.1 | 0.0 | 8.8 | 0.0 | 8.8 |
| C2 | 17.6 | 263.2 | 0.0 | 280.8 | 0.0 | 280.8 |
| C3= | 449.7 | 609.2 | 1.6 | 1057.1 | 0.0 | 629.0 |
| C3 | 136.4 | 228.4 | 127.8 | 235.2 | 0.0 | 235.3 |
| C4= | 14.7 | 0.0 | 14.8 | 0.0 | 0.0 | 0.0 |
| C6=+ | 0.0 | 0.0 | 0.0 | 0.0 | 0.0 | 26.5 |
| DIPE | 0.0 | 0.0 | 0.0 | 0.0 | 5.6 | 190.6 |
| IPA | 0.0 | 0.0 | 0.0 | 0.0 | 134.5 | 139.7 |
| H2O | 0.0 | 0.1 | 0.0 | 0.0 | 247.0 | 56.8 |
| Total | 619.1 | 1109.0 | 144.2 | 1581.9 | 387.1 | 1567.4 |

| Stream No. | R$_x$ Recycle <16A> | C$_2$ Purge <36> | Bottoms <32> | DIPE Raffinate <46> | Water Feed <44> | Stripper Bottoms <52> |
|---|---|---|---|---|---|---|
| C2= | 35.2 | 0.7 | 0.0 | 0.0 | 0.0 | 0.0 |
| C2 | 1123.2 | 17.6 | 0.0 | 0.0 | 0.0 | 0.0 |
| C3= | 2516.0 | 19.2 | 0.6 | 0.6 | 0.0 | 0.0 |
| C3 | 941.2 | 6.5 | 0.3 | 0.3 | 0.0 | 0.0 |
| C4= | 0.0 | 0.0 | 0.0 | 0.0 | 0.0 | 0.0 |
| C6=+ | 106.0 | 0.0 | 26.5 | 26.5 | 0.0 | 0.0 |
| DIPE | 762.4 | 0.0 | 190.6 | 185.0 | 5.5 | 0.0 |
| IPA | 558.8 | 0.0 | 139.7 | 6.0 | 134.1 | 0.5 |
| H2O | 227.2 | 0.0 | 56.7 | 5.8 | 1639.3 | 1487.2 |
| Total | 6269.6 | 44.0 | 414.4 | 224.2 | 1778.9 | 1487.7 |

| Stream No. | Water Feed <42> | Water Feed <54> |
|---|---|---|
| C2= | 0.0 | 0.0 |
| C2 | 0.0 | 0.0 |
| C3= | 0.0 | 0.0 |
| C3 | 0.0 | 0.0 |
| C4= | 0.0 | 0.0 |
| C6=+ | 0.0 | 0.0 |
| DIPE | 0.0 | 0.0 |
| IPA | 0.0 | 0.0 |
| H2O | 101.6 | 94.4 |
| Total | 101.6 | 94.4 |

TABLE 4

Comparison of Column Performance

| Column | P/P Splitter | P/P Stripper | IPA Stripper |
|---|---|---|---|
| Table 1 - Simple purge | | | |
| Oper pressure | 266.0 | 302.0 | 40.0 |
| Diameter | 6.5 | 4.5 | 2.5 |
| Theoretical Stages | 66.0 | 22.0 | 8.0 |
| Cond Temp | 102.0 | 103.0 | — |
| Cond Duty | 15.2 | 10.9 | — |
| Reboil Temp | 134.0 | 317.0 | 268.0 |
| Reboil Duty | 15.3 | 12.7 | 6.1 |
| Reflux Ratio | 1.2 | 1.4 | 0 |
| Table 2 - This invention | | | |
| Oper pressure | 266.0 | 412.0 | 40.0 |
| Diameter | 6.5 | 4.5 | 2.5 |
| Theoretical Stages | 66.0 | 22.0 | 8.0 |
| Cond Temp | 103.0 | 103.0 | — |
| Cond Duty | 22.0 | 9.1 | — |
| Reboil Temp | 132.0 | 355.0 | 268.0 |
| Reboil Duty | 20.9 | 12.5 | 5.9 |
| Reflux Ratio | 1.6 | 75.7 | 0 |
| Table 3 - accumulate C2's | | | |
| Oper pressure | 326.0 | 357.0 | 40.0 |
| Diameter | 11.5 | 4.5 | 2.5 |
| Theoretical Stages | 66.0 | 22.0 | 8.0 |
| Cond Temp | 101.0 | 101.0 | — |
| Cond Duty | 49.3 | 10.5 | — |
| Reboil Temp | 151.0 | 339.0 | 268.0 |
| Reboil Duty | 49.5 | 11.9 | 6.1 |
| Reflux Ratio | 5.0 | 1.0 | 0 |

The unique nature of the DIPE system allows the two significantly different separations, C2/C3 and C3/DIPE, to be performed in the same column with a single reflux. Surprisingly, the high pressure required for condensation of the C2 stream actually slightly improves the ease of the C3/DIPE split. High pressure operation of conventional depropanizers is usually avoided due to convergence of C3 volatilities. This allows the DIPE unit to obtain high propene utilization while processing feeds containing appreciable amounts of C2 - impurities, i.e. 0.1 to 10 wt. %. Use of the P/P splitter to concentrate the recycled propene allows for easy rejection of any C4+material in the fresh feed. Depending on the C4 content, the fresh feed may be processed by the initial P/P splitter unit or sent directly to the reactor.

Limitations on water miscibility, performance, blended gasoline product vapor pressure (RVP), and corrosion make the ether the preferred fuel blending component for oxygenate and octane requirements over the alcohol. Due to the relatively high IPA content in the DIPE azeotrope, extraction is the preferred method of meeting limitations on alcohol content (typically 2%) for pipeline transport. In addition, recycling the alcohol is critical for maintaining single phase operation and extending catalyst life. Location of the water makeup and operation of the IPA stripper is critical to balance the IPA production with IPA losses from the system while maintaining single phase operation. The IPA/H2O ratio affects both the phase equilibria (IPA is a cosolvent for water in hydrocarbons) and the chemical reaction equilibria (H2O favors IPA production over DIPE).

Accordingly, an improved process is provided for production of fuel grade DIPE from low purity commercial feedstocks. This process offers significant advantages in catalyst life, propene utilization, capital cost, utility consumption and the ability to process impure feedstocks. Advantages of the process comprise: 1) reduction of reactor water content, 2) oxidative catalyst regeneration, 3) in-situ concentration and rejection of C2-, and C4+ feed impurities, 4) extraction of IPA, and 5) distillation and recycle of IPA to extinction.

While the invention has been described by specific examples and embodiments, there is no intent to limit the inventive concept except as set forth in the following claims.

We claim:

1. In the process for the production of diisopropyl ether by hydration and etherification of hydrocarbon feedstock containing propene, propane and $C_2$- light gas components, which comprises contacting the feedstock and water in a catalytic reactor containing porous solid acidic olefin hydration catalyst under olefin hydration and etherification conditions, the improvement which comprises:
   recovering a net liquid effluent stream from said catalytic reactor containing diisopropyl ether, isopropanol, water, unreacted propene, propane and $C_2$- light gas components;
   separating at least a portion of said liquid effluent stream in a vertical stripper column having a lower reboiler portion and an upper contact portion;
   recovering an overhead vapor stream containing propene, propane and $C_2$- light gas components from the stripper column;
   cooling the overhead vapor stream to provide a condensed reflux stream rich in propene and propane;
   removing the $C_2$- light gas components from the condensed reflux stream;
   recycling the reflux stream to the upper contact portion of the stripper column;
   recovering a predominantly C3 recycle stream from the upper contact portion of the stripper column; and
   passing at least a portion of the C3 recycle stream to the catalytic reactor.

2. The process of claim 1 including the step of prefractionating fresh feedstock containing propene, propane and $C_2$- light gas components to provide a reactor feedstream rich in propene and containing 0.1 to 10 wt. % $C_2$- components.

3. The process of claim 2 wherein at least a portion of the C3 recycle stream is prefractionated with fresh feedstock.

4. The process of claim 1 including the step of splitting the liquid effluent stream into a liquid product recovery stream and a liquid recycle stream;
   cooling at least a portion of said liquid recycle stream; and
   passing said cooled liquid recycled stream as interstage quench between serial fixed bed hydration zones in said catalytic reactor for controlling reaction temperature, wherein total liquid recycle is combined with fresh feed at a weight ratio of 2:1 to 10:1 recycle:feed.

5. The process of claim 4 wherein said liquid product stream is separated into at least two streams for recycle to separate reaction zones, and wherein at least a portion of cooled liquid recycle is injected between separated fixed catalyst beds.

6. The process of claim 4 wherein said fixed bed zones are maintained in a vertical downflow reactor; and wherein the solid catalyst comprises at least one acidic zeolite.

7. The process of claim 1 wherein said solid catalyst comprises zeolite Beta, and wherein the hydration zone conditions comprise temperature of 100° to 250° C.

8. A process for production of diisopropyl ether by conversion of hydrocarbon feedstock containing propene, propane and $C_2$- light gas components, including the steps of:
   prefractionating fresh feedstock containing propene, propane and $C_2$- light gas components to provide a reactor feedstream rich in propene;
   contacting the feedstock and water in a catalytic reactor with acidic catalyst under olefin hydration and etherification conditions;
   recovering from the catalytic reactor a liquid reactor effluent stream containing diisopropyl ether, isopropanol, water, unreacted propene, propane and $C_2$- light gas components;
   splitting the liquid reactor effluent stream into a liquid product recovery stream and a liquid recycle stream;
   separating the liquid product recovery stream in a vertical stripper column;
   recovering an overhead vapor stream containing propene, propane and $C_2$- light gas components from the stripper column;
   cooling the overhead vapor stream to provide a reflux stream rich in condensed propene and propane;
   removing the $C_2$- light gas components form condensed;
   recycling the reflux stream to an upper contact portion of the stripper column;
   recovering a predominantly C3 recycle stream form the upper contact portion of the stripper column; and
   passing substantially the entire the C3 recycle stream to the to the prefractioning step for propene enrichment with fresh feedstock.

9. A process of claim 8 wherein the liquid product recovery stream consists essentially of 0.5-10 wt. % water, 20-60 wt. % propene, 20-30 wt. % di-isopropyl ether, 10-15 wt. % isopropanol, and 5 to 40 wt. % total propane and $C_2$- components.

10. The process of claim 8 wherein the catalyst comprises porous zeolite having a pore size of 5-8 Angstroms, and reaction temperature is maintained at 100° to 250° C.

11. The process of claim 8 including the steps of recovering form the stripper column a liquid bottom stream containing diisopropyl ether and isopropanol; extracting isopropanol form said liquid stripper bottom stream with a supercritical extractant to provide a raffinate stream rich in diisopropyl ether.

12. The process of claim 11 wherein extracted isopropanol is recycled to the catalytic reactor for conversion to ether.

13. The process of claim 8 wherein the liquid product recovery stream consists essentially of 0.5-10 wt. % water, 20-60 wt. % propene, 20-30 wt. % di-isopropyl ether, 10-15 wt. % isopropanol, at least 5 wt. % propane and 0.1 to 10 wt. % $C_2$- components.

14. A process for production of diisopropyl ether by conversion of hydrocarbon feedstock containing propene, propane and $C_2$- light gas components, including the steps of:

prefractionating fresh feedstock containing propene, propane and $C_2$- light gas components to provide a reactor feedstream rich in propene;

contacting the feedstock and water in a catalytic reactor with acidic catalyst under olefin hydration and etherification reaction conditions, wherein the catalyst comprises porous zeolite having a pore size of 5-8 Angstroms, and reaction temperature is maintained at 100° to 250° C.;

recovering form the catalytic reactor a liquid reactor effluent stream containing 0.5-10 wt. % water, 20-60 wt. % propene, 20-30 wt. % di-isopropyl ether, 10-15 wt. % isopropanol, at least 5 wt. % total propane, and 0.1 to 10 wt. % $C_2$- components;

separating at least a portion of the liquid reactor effluent stream in a vertical stripper column;

recovering an overhead vapor stream containing propene, propane and $C_2$- light gas components from the stripper column;

cooling the overhead vapor stream to provide a reflux stream rich in condensed propene and propane;

removing the $C_2$- light gas components for condensed;

recycling the reflux stream to an upper contact portion of the stripper column;

recovering a predominantly C3 recycle stream from the upper contact portion of the stripper column; and passing substantially the entire the C3 recycle stream to the prefractioning step for propene enrichment with fresh feedstock.

* * * * *